US009371525B2

(12) United States Patent
Urech

(10) Patent No.: US 9,371,525 B2
(45) Date of Patent: Jun. 21, 2016

(54) FUNCTIONALIZED POLYPEPTIDES

(71) Applicant: ESBATech, an Alcon Biomedical Research Unit LLC, Schlieren (CH)

(72) Inventor: David Urech, Hombrechtikon (CH)

(73) Assignee: Esbatech, an Alcon Biomedical Reseach Unit LLC, Schlieren (CH)

(*) Notice: Subject to any disclaimer, the term of this patent is extended or adjusted under 35 U.S.C. 154(b) by 78 days.

(21) Appl. No.: 14/134,988

(22) Filed: Dec. 19, 2013

(65) Prior Publication Data

US 2014/0178386 A1   Jun. 26, 2014

Related U.S. Application Data

(62) Division of application No. 13/000,499, filed as application No. PCT/CH2009/000225 on Jun. 30, 2009, now Pat. No. 8,637,022.

(60) Provisional application No. 61/076,775, filed on Jun. 30, 2008.

(51) Int. Cl.
| | |
|---|---|
| A61K 38/00 | (2006.01) |
| C12N 15/10 | (2006.01) |
| A61K 47/48 | (2006.01) |
| C07K 16/00 | (2006.01) |
| C07K 16/24 | (2006.01) |

(52) U.S. Cl.
CPC ...... *C12N 15/1062* (2013.01); *A61K 47/48215* (2013.01); *A61K 47/48338* (2013.01); *C07K 16/00* (2013.01); *C07K 16/241* (2013.01); *C12N 15/1037* (2013.01); *C07K 2317/41* (2013.01); *C07K 2319/31* (2013.01)

(58) Field of Classification Search
None
See application file for complete search history.

(56) References Cited

U.S. PATENT DOCUMENTS

| | | | |
|---|---|---|---|
| 6,258,558 B1 | 7/2001 | Szostak et al. | |
| 6,492,123 B1 * | 12/2002 | Holliger et al. | 435/7.1 |
| 6,653,285 B1 | 11/2003 | Takashima et al. | |
| 6,699,658 B1 | 3/2004 | Wittrup | |
| 6,803,438 B1 | 10/2004 | Brocchini et al. | |
| 7,045,337 B2 | 5/2006 | Schultz et al. | |
| 7,083,970 B2 | 8/2006 | Schultz et al. | |
| 7,118,879 B2 | 10/2006 | Ladner et al. | |
| 7,211,395 B2 | 5/2007 | Sato et al | |
| 8,349,322 B2 | 1/2013 | Borras et al. | |
| 2004/0037834 A1 | 2/2004 | Woloski et al. | |
| 2005/0159343 A1 | 7/2005 | Takashima et al. | |
| 2006/0239965 A1 | 10/2006 | Szoka, Jr. et al. | |
| 2007/0009987 A1 | 1/2007 | Choe et al. | |
| 2007/0092940 A1 | 4/2007 | Eigenbrot et al. | |
| 2007/0202045 A1 | 8/2007 | Dennis | |

FOREIGN PATENT DOCUMENTS

| | | |
|---|---|---|
| EP | 1222217 B1 | 6/2005 |
| EP | 1240337 B1 | 8/2006 |
| EP | 1701741 B1 | 5/2008 |
| EP | 1648518 B1 | 8/2009 |
| WO | 0117515 A1 | 3/2001 |
| WO | 0180899 A | 11/2001 |
| WO | 02076489 A1 | 10/2002 |
| WO | 03059973 A2 | 7/2003 |
| WO | 03089010 A1 | 10/2003 |
| WO | 03097697 A2 | 11/2003 |
| WO | 2004056852 A2 | 7/2004 |
| WO | 2005007197 A2 | 1/2005 |
| WO | 2005065712 A2 | 7/2005 |
| WO | 2006008096 A1 | 1/2006 |
| WO | 2006036834 A2 | 4/2006 |
| WO | 2006131013 A2 | 12/2006 |
| WO | 2007038619 A2 | 4/2007 |
| WO | 2007146968 A2 | 12/2007 |
| WO | 2008006235 A2 | 1/2008 |
| WO | 2009000098 A2 | 12/2008 |
| WO | 2009000099 A | 12/2008 |

OTHER PUBLICATIONS

Rajendra et al. (The EMBO Journal, 1995, 14:2987-2998).*
Albrecht (Bioconjugate Chem, 2004, 15:16-26).*
Matthias Mack, et al.; "A small bispecific antibody construct expressed as a functional single-chain molecule with high tumor cell cytotoxicity"; Immunology; Jul. 1995; pp. 7021-7025; vol. 92; Proc. Natl. Acad. Sci. USA.
Huguette Albrecht, et al.; Journal of Immunological Methods; (2006); pp. 100-116; Elsevier (online).
Search Report corresponding to PCT Application Serial No. PCT/CH09/000225, Publication No. WO/2010/006454, dated Feb. 5, 2010.
Written Opinion corresponding to PCT Application Serial No. PCT/CH09/000225, Publication No. WO/2010/006454, dated Dec. 31, 2010.
Baeuerle and Reinhardt; "Bispecific T-cell engaging antibodies for cancer therapy"; Cancer Research; vol. 69; pp. 4941-4944 (Jun. 9, 2009).
Berge et al.; "Pharmaceutical salts" Review Article; Journal of Pharmaceutical Sciences; vol. 66; No. 1; pp. 2-19 (Jan. 1977).
Bird et al; "Single-chain antigen-binding proteins"; Science; vol. 242; pp. 423-426; (Oct. 21, 1988).
Brocchini et al.; "PEGylation of native disulfide bonds in proteins"; Nature Protocols; vol. 1; No. 5; pp. 2241-2252 (2006).
Huston et al; "Protein engineering of antibody binding sites: recovery of specific activity in an anti-digoxin single-chain Fv analogue produced in *Escherichia coli*"; Proc. natl. Acad. Sci.; vol. 85; pp. 5879-5883 (Aug. 1988).

(Continued)

*Primary Examiner* — Sean Aeder
*Assistant Examiner* — Julie Wu
(74) *Attorney, Agent, or Firm* — Jason J. Derry

(57) ABSTRACT

The invention provides functionalized polypeptides, especially therapeutic polypeptides (e.g., scFv), comprising a linker sequence that can be rapidly and specifically functionalized by the addition of one or functional moieties (e.g., PEG) or binding specificities (e.g., an amino acid sequence with a particular binding specificity). Such functionalized polypeptides are advantageous in that they have improved pharmacokinetic properties (e.g., improved in vivo half-life, tissue penetration and tissue residency time) over non-functionalized polypeptides. Methods for the rapid and reproducible generation of functionalized polypeptides are also provided.

17 Claims, 7 Drawing Sheets

(56) References Cited

OTHER PUBLICATIONS

Shaunak et al.; "Site-specific PEGylation of native disulfide bonds in therapeutic proteins"; Brief Communications; Nature Chemical Biology; vol. 2; No. 6; pp. 312-313 (Jun. 2006).

Skerra and Pluckthun; "Assembly of a functional immunoglobulin Fv fragment in *Escherichia coli*"; Science; vol. 240; pp. 1038-1041 (May 20, 1988).

Vita; "Engineering novel proteins by transfer of active sites to natural scaffolds"; Current Opininion Biotechnology; vol. 8; No. 4; pp. 429-434 (1997).

Carter; "Potent antibody therapeutics by design"; Nature Reviews; Immunology, Nature Publishing; vol. 6; pp. 343-357 (Apr. 7, 2006).

Mummert et al; "Development of a peptide inhibitor of hyaluronan-mediated leukocyte trafficking"; Journal of Experimetnal Medicine; vol. 192; No. 6; pp. 769-779 (Sep. 19, 2000).

Zanetti, et al.; Expression of conformationally constrained adhesion peptide in an antibody CDR loop and inhibition of natural killer cell cytotoxic activity by an antibody antigenized with the RGD motif; EMBO Journal; vol. 12; No. 11; pp. 4375-4384 (Jan. 1, 1993).

Search Report and Written Opinion from corresponding PCT Application Serial No. CH2008000285, (2009).

* cited by examiner

SEQUENCE LISTING

```
<160> NUMBER OF SEQ ID NOS: 8

<210> SEQ ID NO 1
<211> LENGTH: 83
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: X can be any naturally occurring amino acid.
      at least three and up to 15 amino acids can be present
<220> FEATURE:
<221> NAME/KEY: MISC_FEATURE
<222> LOCATION: (17)..(66)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (69)..(83)
```

<223> OTHER INFORMATION: X can be any naturally occurring amino acid.
      at least three and up to 15 amino acids can be present

<400> SEQUENCE: 1

Xaa Xaa Xaa Xaa Xaa Xaa Xaa Xaa Xaa Xaa Xaa Xaa Xaa Xaa Cys
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Cys Gly Xaa Xaa Xaa Xaa Xaa Xaa Xaa Xaa Xaa Xaa Xaa
65                  70                  75                  80

Xaa Xaa Xaa

<210> SEQ ID NO 2
<211> LENGTH: 72
<212> TYPE: PRT
<213> ORGANISM: Artificial
<220> FEATURE:
<223> OTHER INFORMATION: linker sequence
<220> FEATURE:
<221> NAME/KEY: MISC_FEATURE
<222> LOCATION: (12)..(61)
<223> OTHER INFORMATION: X can be any naturally occurring amino acid.
      at least three and up to 50 amino acids can be present

<400> SEQUENCE: 2

Gly Gly Gly Gly Ser Gly Gly Gly Ser Cys Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Cys Gly Gly
    50                  55                  60

Gly Gly Ser Gly Gly Gly Gly Ser
65                  70

<210> SEQ ID NO 3
<211> LENGTH: 29
<212> TYPE: PRT
<213> ORGANISM: Artificial Sequence
<220> FEATURE:
<223> OTHER INFORMATION: linker sequence

<400> SEQUENCE: 3

Gly Gly Gly Gly Ser Gly Gly Gly Ser Cys Gly Gly Ser Gly
1               5                   10                  15

Gly Gly Cys Gly Gly Gly Gly Ser Gly Gly Gly Gly Ser
            20                  25

<210> SEQ ID NO 4
<211> LENGTH: 34
<212> TYPE: PRT
<213> ORGANISM: Artificial Sequence
<220> FEATURE:
<223> OTHER INFORMATION: linker sequence

<400> SEQUENCE: 4

Gly Gly Gly Gly Ser Gly Gly Gly Gly Ser Cys Gly Ala His Trp Gln

```
                1               5                  10                  15

Phe Asn Ala Leu Thr Val Arg Cys Gly Gly Gly Ser Gly Gly Gly
                            20                  25                  30

Gly Ser

<210> SEQ ID NO 5
<211> LENGTH: 252
<212> TYPE: PRT
<213> ORGANISM: Artificial Sequence
<220> FEATURE:
<223> OTHER INFORMATION: scFv ESBA903

<400> SEQUENCE: 5

Met Glu Ile Val Met Thr Gln Ser Pro Ser Thr Leu Ser Ala Ser Val
1               5                   10                  15

Gly Asp Arg Val Ile Ile Thr Cys Gln Ala Ser Glu Ile Ile His Ser
                20                  25                  30

Trp Leu Ala Trp Tyr Gln Gln Lys Pro Gly Lys Ala Pro Lys Leu Leu
            35                  40                  45

Ile Tyr Leu Ala Ser Thr Leu Ala Ser Gly Val Pro Ser Arg Phe Ser
        50                  55                  60

Gly Ser Gly Ser Gly Ala Glu Phe Thr Leu Thr Ile Ser Ser Leu Gln
65                  70                  75                  80

Pro Asp Asp Phe Ala Thr Tyr Tyr Cys Gln Asn Val Tyr Leu Ala Ser
                85                  90                  95

Thr Asn Gly Ala Asn Phe Gly Gln Gly Thr Lys Leu Thr Val Leu Gly
                100                 105                 110

Gly Gly Gly Gly Ser Gly Gly Gly Ser Gly Gly Gly Gly Ser Gly
            115                 120                 125

Gly Gly Gly Ser Glu Val Gln Leu Val Glu Ser Gly Gly Gly Leu Val
            130                 135                 140

Gln Pro Gly Gly Ser Leu Arg Leu Ser Cys Thr Ala Ser Gly Phe Ser
145                 150                 155                 160

Leu Thr Asp Tyr Tyr Met Thr Trp Val Arg Gln Ala Pro Gly Lys
                165                 170                 175

Gly Leu Glu Trp Val Gly Phe Ile Asp Pro Asp Asp Asp Pro Tyr Tyr
            180                 185                 190

Ala Thr Trp Ala Lys Gly Arg Phe Thr Ile Ser Arg Asp Thr Ser Lys
            195                 200                 205

Asn Thr Val Tyr Leu Gln Met Asn Ser Leu Arg Ala Glu Asp Thr Ala
        210                 215                 220

Val Tyr Tyr Cys Ala Gly Gly Asp His Asn Ser Gly Trp Gly Leu Asp
225                 230                 235                 240

Ile Trp Gly Gln Gly Thr Leu Val Thr Val Ser Ser
                245                 250

<210> SEQ ID NO 6
<211> LENGTH: 266
<212> TYPE: PRT
<213> ORGANISM: Artificial Sequence
<220> FEATURE:
<223> OTHER INFORMATION: scFv ESBA903 with SS linker

<400> SEQUENCE: 6

Met Glu Ile Val Met Thr Gln Ser Pro Ser Thr Leu Ser Ala Ser Val
1               5                   10                  15

Gly Asp Arg Val Ile Ile Thr Cys Gln Ala Ser Glu Ile Ile His Ser
```

```
            20                  25                  30
Trp Leu Ala Trp Tyr Gln Gln Lys Pro Gly Lys Ala Pro Lys Leu Leu
            35                  40                  45

Ile Tyr Leu Ala Ser Thr Leu Ala Ser Gly Val Pro Ser Arg Phe Ser
        50                  55                  60

Gly Ser Gly Ser Gly Ala Glu Phe Thr Leu Thr Ile Ser Ser Leu Gln
65                  70                  75                  80

Pro Asp Asp Phe Ala Thr Tyr Tyr Cys Gln Asn Val Tyr Leu Ala Ser
                85                  90                  95

Thr Asn Gly Ala Asn Phe Gly Gln Gly Thr Lys Leu Thr Val Leu Gly
            100                 105                 110

Gly Gly Gly Gly Ser Gly Gly Gly Ser Cys Gly Ala His Trp Gln
            115                 120                 125

Phe Asn Ala Leu Thr Val Arg Cys Gly Gly Gly Ser Gly Gly Gly
            130                 135                 140

Gly Ser Glu Val Gln Leu Val Glu Ser Gly Gly Leu Val Gln Pro
145                 150                 155                 160

Gly Gly Ser Leu Arg Leu Ser Cys Thr Ala Ser Gly Phe Ser Leu Thr
                165                 170                 175

Asp Tyr Tyr Tyr Met Thr Trp Val Arg Gln Ala Pro Gly Lys Gly Leu
            180                 185                 190

Glu Trp Val Gly Phe Ile Asp Pro Asp Asp Pro Tyr Tyr Ala Thr
            195                 200                 205

Trp Ala Lys Gly Arg Phe Thr Ile Ser Arg Asp Thr Ser Lys Asn Thr
        210                 215                 220

Val Tyr Leu Gln Met Asn Ser Leu Arg Ala Glu Asp Thr Ala Val Tyr
225                 230                 235                 240

Tyr Cys Ala Gly Gly Asp His Asn Ser Gly Trp Gly Leu Asp Ile Trp
                245                 250                 255

Gly Gln Gly Thr Leu Val Thr Val Ser Ser
            260                 265

<210> SEQ ID NO 7
<211> LENGTH: 247
<212> TYPE: PRT
<213> ORGANISM: Artificial Sequence
<220> FEATURE:
<223> OTHER INFORMATION: scFv ESBA105

<400> SEQUENCE: 7

Met Ala Asp Ile Val Met Thr Gln Ser Pro Ser Ser Leu Ser Ala Ser
1               5                   10                  15

Val Gly Asp Arg Val Thr Leu Thr Cys Thr Ala Ser Gln Ser Val Ser
            20                  25                  30

Asn Asp Val Val Trp Tyr Gln Gln Arg Pro Gly Lys Ala Pro Lys Leu
            35                  40                  45

Leu Ile Tyr Ser Ala Phe Asn Arg Tyr Thr Gly Val Pro Ser Arg Phe
        50                  55                  60

Ser Gly Arg Gly Tyr Gly Thr Asp Phe Thr Leu Thr Ile Ser Ser Leu
65                  70                  75                  80

Gln Pro Glu Asp Val Ala Val Tyr Tyr Cys Gln Asp Tyr Asn Ser
                85                  90                  95

Pro Arg Thr Phe Gly Gln Gly Thr Lys Leu Glu Val Lys Arg Gly Gly
            100                 105                 110

Gly Gly Ser Gly Gly Gly Gly Ser Gly Gly Gly Gly Ser Ser Gly Gly
```

```
            115                 120                 125
Gly Ser Gln Val Gln Leu Val Gln Ser Gly Ala Glu Val Lys Lys Pro
    130                 135                 140

Gly Ala Ser Val Lys Val Ser Cys Thr Ala Ser Gly Tyr Thr Phe Thr
145                 150                 155                 160

His Tyr Gly Met Asn Trp Val Arg Gln Ala Pro Gly Lys Gly Leu Glu
                165                 170                 175

Trp Met Gly Trp Ile Asn Thr Tyr Thr Gly Glu Pro Thr Tyr Ala Asp
            180                 185                 190

Lys Phe Lys Asp Arg Phe Thr Phe Ser Leu Glu Thr Ser Ala Ser Thr
        195                 200                 205

Val Tyr Met Glu Leu Thr Ser Leu Thr Ser Asp Asp Thr Ala Val Tyr
    210                 215                 220

Tyr Cys Ala Arg Glu Arg Gly Asp Ala Met Asp Tyr Trp Gly Gln Gly
225                 230                 235                 240

Thr Leu Val Thr Val Ser Ser
                245

<210> SEQ ID NO 8
<211> LENGTH: 256
<212> TYPE: PRT
<213> ORGANISM: Artificial Sequence
<220> FEATURE:
<223> OTHER INFORMATION: scFv ESBA105 with SS linker

<400> SEQUENCE: 8

Met Ala Asp Ile Val Met Thr Gln Ser Pro Ser Ser Leu Ser Ala Ser
1               5                   10                  15

Val Gly Asp Arg Val Thr Leu Thr Cys Thr Ala Ser Gln Ser Val Ser
            20                  25                  30

Asn Asp Val Val Trp Tyr Gln Gln Arg Pro Gly Lys Ala Pro Lys Leu
        35                  40                  45

Leu Ile Tyr Ser Ala Phe Asn Arg Tyr Thr Gly Val Pro Ser Arg Phe
    50                  55                  60

Ser Gly Arg Gly Tyr Gly Thr Asp Phe Thr Leu Thr Ile Ser Ser Leu
65                  70                  75                  80

Gln Pro Glu Asp Val Ala Val Tyr Tyr Cys Gln Gln Asp Tyr Asn Ser
                85                  90                  95

Pro Arg Thr Phe Gly Gln Gly Thr Lys Leu Glu Val Lys Arg Gly Gly
            100                 105                 110

Gly Gly Ser Gly Gly Gly Gly Ser Cys Gly Gly Gly Ser Gly Gly Gly
        115                 120                 125

Cys Gly Gly Gly Ser Gly Gly Gly Ser Gln Val Gln Leu Val
    130                 135                 140

Gln Ser Gly Ala Glu Val Lys Lys Pro Gly Ala Ser Val Lys Val Ser
145                 150                 155                 160

Cys Thr Ala Ser Gly Tyr Thr Phe Thr His Tyr Gly Met Asn Trp Val
                165                 170                 175

Arg Gln Ala Pro Gly Lys Gly Leu Glu Trp Met Gly Trp Ile Asn Thr
            180                 185                 190

Tyr Thr Gly Glu Pro Thr Tyr Ala Asp Lys Phe Lys Asp Arg Phe Thr
        195                 200                 205

Phe Ser Leu Glu Thr Ser Ala Ser Thr Val Tyr Met Glu Leu Thr Ser
    210                 215                 220
```

```
Leu Thr Ser Asp Asp Thr Ala Val Tyr Tyr Cys Ala Arg Glu Arg Gly
225                 230                 235                 240

Asp Ala Met Asp Tyr Trp Gly Gln Gly Thr Leu Val Thr Val Ser Ser
                245                 250                 255
```

FUNCTIONALIZED POLYPEPTIDES

RELATED APPLICATIONS

The present application is a divisional of U.S. application Ser. No. 13/000,499 filed Dec. 21, 2010 (now allowed) which claims priority from PCT/CH2009/000225, filed Jun. 30, 2009, which claims priority to U.S. Provisional Application Ser. No. 61/076,775, filed Jun. 30, 2008, the contents of which are hereby incorporated by reference in their entireties.

BACKGROUND INFORMATION

The efficacy of therapeutic polypeptides is often greatly limited by their intrinsic pharmacokinetic properties. For example, in the case of therapeutic antibodies, problems with tissue penetration, tissue residency and serum half-life are frequently reported. Improvements in the pharmacokinetic properties of a therapeutic polypeptide can result in improved efficacy and reduced dosing regimes. Current methods of modulating the pharmacokinetic properties of therapeutic polypeptides are typically limited to addressing the issue of serum half-life. Moreover these methods typically involve time consuming or non-specific chemical alteration of existing polypeptides.

Accordingly, there is a need in the art for improved methods of modulating the pharmacokinetic properties of therapeutic polypeptides that provide a rapid and specific means of amino acid modification, and that address pharmacokinetic parameters in addition to half-life.

SUMMARY OF THE INVENTION

The invention provides functionalized polypeptides, especially therapeutic polypeptides (e.g., scFv). The polypeptides of the invention comprise a linker sequence that can be rapidly and specifically functionalized by the addition of one or functional moieties (e.g., PEG) and/or binding specificities (e.g., an amino acid sequence with a particular binding specificity). Such functionalized polypeptides are advantageous in that they have improved pharmacokinetic properties (e.g., improved in vivo half-life, tissue penetration and tissue residency time) over non-functionalized polypeptides. Methods for the rapid and reproducible generation of functionalized polypeptides are also provided.

Accordingly, in one aspect, the invention provides a polypeptide, such as an immunobinder (e.g. a scFv), comprising two domains connected by an amino acid linker. The linker generally comprises two cysteines capable of forming an intrachain disulphide bond, and the amino acids in the linker sequence between these two cysteines form a loop when the two cysteines are disulphide bonded to one another. In a particular embodiment, the linker comprises sequence set forth in SEQ ID No:1 or 2.

In certain embodiments, the linker contains a loop that binds to a target molecule, such as a PK modifier (e.g., hyaluronic acid, and serum albumin). By binding to the target molecule, the serum half-life and/or the penetration efficacy into tissues and/or particular binding specificity of the linker comprising polypeptide is enhanced. In a particular embodiment, the linker comprises the amino acid sequence set forth in SEQ ID No:3 or 4. In a preferred embodiment, the polypeptide comprises the amino acid sequence set forth in SEQ ID No. 6 or 8.

In certain embodiments, at least one cysteine residue in the linker is covalently linked to a functional moiety. In a particular embodiment, two cysteine residues in the linker are covalently linked to the same functional moiety. Suitable functional moieties include, for example, PEG, carbohydrate molecules and hydroxyethyl starch (HES). Upon covalent linkage of a functional moiety such as PEG or HES to a polypeptide, the half-life of such polypeptide within a subject is prolonged.

In another aspect, the invention provides compositions comprising one or more polypeptides of the invention and a pharmaceutically acceptable carrier.

In other aspects, the invention provides nucleic acid molecules (e.g. vectors) encoding the polypeptides of the invention, and host cells containing such nucleic acid molecules.

In another aspect, the invention provides methods producing a functionalized polypeptide. Such methods generally involve providing a library of peptide sequences, identifying from the library at least one peptide sequence that bind to a target molecule, and modifying the loop region of a linker-containing polypeptide to comprise at least one peptide sequence identified. Desired peptide sequences can be identified by any art recognized means, including, for example, phage display, yeast display, or mRNA display.

DESCRIPTION OF THE DRAWINGS

FIG. 1 depicts an SDS page of variously treated ESBA105 molecules (lanes 3-10). Lane 1: Marker; lane 2: not specified; lane 3: reduced with DTT; lane 4: reduced and dialyzed; lane 5: reduced, cysteine-PEGylated; lane 6: cysteine-PEGylated, dialyzed; lane 7: Control; lane 8: Lysine-PEGylated; lane 9: Laysine-PEGylated, dialysed; lane: 10 control. The molecular size of PEG was aprox. 0.7 kDa/PEG.

FIG. 2 shows ELISA analysis of the TNFalpha binding-activity of (A) cysteine-PEGylated ESBA105 and (B) lysine-PEGylated ESBA105. A: The EC50 for ESBA105 was 0.9833; for reduced ESBA105: 1.291; and for Cys pegylated ESBA105: 1.164. $R^2$ for ESBA105 was 0.9814; for reduced ESBA105: 0.9891; Cys pegylated ESBA105: 0.9857. B: The EC50 for ESBA105 was 0.8073 and for Lys pegylated ESBA105: 1.326. $R^2$ for ESBA105 was 0.9870 and for pegylated ESBA105 0.9640.

FIG. 3 shows (a) a schematic of unmodified, oxidized ESBA105-SS-linker, (b) ESBA105-SS-linker PEGylated (ESBA105-$S_2$—$PEG_2$) using a monofunctional PEGylating reagent 1, and (c) ESBA105-SS-linker PEGylated (ESBA105-$S_2$—PEG) using a bifunctional PEGylating reagent 2.

FIG. 4 shows: (A) ELISA analysis of the TNFalpha binding-activity of ESBA105 and ESBA105-SS-linker; (B) an SDS-PAGE gel of ESBA105 subjected to various treatments; and, (C) a Western blot assessing the extent of PEGylation of ESBA105 and ESBA105-SS-linker using a rabbit anti-PEG antibody. FIG. 4 (B): lane 1: ESBA105 SS linker reduced+dialyzed+up-concentrated; lane 2: ESBA105 SS linker reduced+dialyzed; lane 3: ESBA105 SS linker reduced+pegylated; lane 4: ESBA105 SS linker reduced+pegylated+dialyzed; lane 5: ESBA105 SS linker.

FIG. 5 shows a schematic illustrating the presentation of the peptide loop of an scFv molecule 1 on the surface of a bacteriophage 2 for the purposes of phage display (the scFv molecule and the phage are not to scale). In the depicted case, the loop comprises 7 amino acids which may interact with a target molecule 3 such as serum albumin (half live prolongation), FcRx (placenta transport), Mucin (epithelial residence time prolongation), Integrin (RGD peptides), Complement, Tight-junction proteins, Multimerization, etc.

FIG. 6 shows ELISA analysis of the TNFalpha binding-activity of ESBA105 and cysteine-PEGylated ESBA105-SSlinker. The EC50 for ESBA105 was 0.9980; and for ESBA105 with pegylated SS linker: 1.181. $R^2$ was for ESBA105 0.9397; and for ESBA105 with pegylated SS linker: 0.9851.

Figure 7:
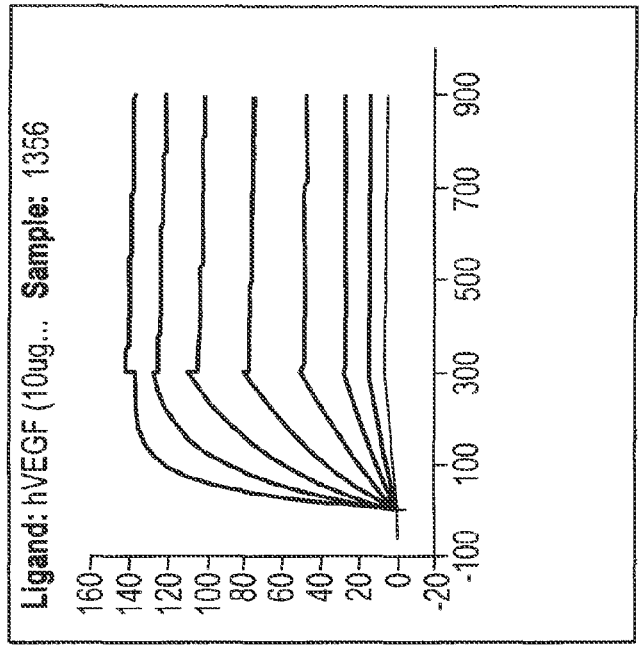
Figure 7:
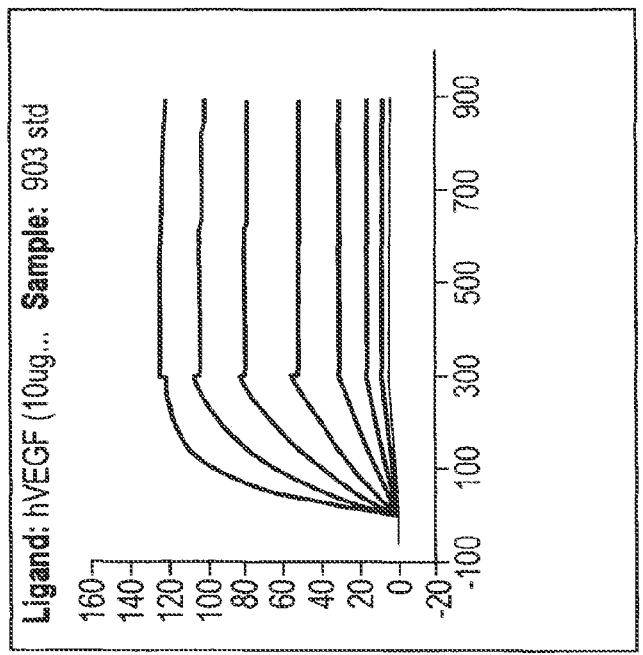

FIG. 7a shows the VEGF binding kinetics of ESBA903. Fit: 1:1 binding; ka (1/Ms): 7.68E+5; kd (1/s): 4.310E−5; KD (M): 5.608E−11. FIG. 7b shows the binding kinetics of ESBA903-Pep1. Fit: 1:1 binding; ka (1/Ms): 1.133E+6; kd (1/s): 5.026E−5. For both, 7a and 7b, the values of the X-axis are given in seconds, the values of the Y-axis are given in resonance units (RU).

DETAILED DESCRIPTION

Definitions

The term "domain", with respect to a polypeptide, takes its art recognized meaning and refers a discrete unit of tertiary structure. Examples of domains include, without limitation, antibody VH or VL domains, fibronectin domains and ankyrin-repeat domains.

The term "linker" refers to a linear amino acid sequence linking two domains. Linkers of the invention can be genetically and/or chemically fused to a domain. In certain embodiments, linkers contain a loop.

The term "loop" refers to a cyclical amino acid sequence formed by an intrachain disulphide bond within a linker.

The term "polyethylene glycol" or "PEG" refers to a linear or branched neutral polyether with the chemical formula $HO-(CH_2CH_2O)_n-H$, and reactive derivatives thereof. Reactive PEG derivatives are well known in the art and include, without limitation, PEG coupled to methyl-PEO12-maleimide, N-hydroxy succinimidyl carbonate, N-hydroxy succinimidyl propionate, p-nitrophenyl-carbonate, benzotriazole-carbonate, and an aldehyde. In a particular embodiment, the amino-reactive PEG derivative is a bis-sulfone-coupled PEG capable of reacting specifically with disulphide bonds (see e.g., Brocchini et al, Nature Protocols, 2006: 1(5), 241). Suitable PEG molecules are of a molecular size between 0.5 kDa and 50 kDa.

The term "target molecule" refers to any molecule specifically bound by the loop region of a polypeptide of the invention. Target molecules, include, for example, sugars, proteins and lipids.

The term "functional moiety" refers to a biological or chemical entity that imparts additional functionality to a molecule to which it is attached (e.g. a PEG molecule, one or more carbohydrate molecules or hydroxyethyl starch (HES)).

The term "PK modifier" refers to any molecule that alters the pharmacokinetic profile of a protein when bound to that protein. A PK modifier is typically, but not necessarily, a naturally occurring, endogenous molecule present in a subject (e.g. a patient). The localization and abundance of such PK modifier within a subject can be physiological or pathological (e.g. overexpressed on the surface of cancer cells, or at an inflamed site). Suitable PK modifiers include, for example, hyaluronic acid, collagen type II, serum albumin, antibody Fc receptors (e.g., FcRx), antibody Fc regions, mucins, integrins, tight junction proteins, transferrin, and complement factors.

The term "modified" or "modifying", with respect to the amino acid sequence of a polypeptide, refers to both the addition of amino acids into the polypeptide sequence or the substitution of existing amino acids in the polypeptide sequence. Amino acids suitable for modifying a polypeptide include all known natural amino acids, unnatural amino acids, and functionalized derivatives thereof (see. e.g., U.S. Pat. Nos. 7,045,337 and 7,083,970 which are hereby incorporate by reference in their entireties).

The term "immunobinder" refers to a molecule that contains all or a part of the antigen binding site of an antibody, e.g., all or part of the heavy and/or light chain variable domain, such that the immunobinder specifically recognizes a target antigen. Non-limiting examples of immunobinders include full-length immunoglobulin molecules and scFvs, as well as antibody fragments, including but not limited to (i) a Fab fragment, a monovalent fragment consisting of the $V_L$, $V_H$, $C_L$ and $C_H 1$ domains; (ii) a F(ab')$_2$ fragment, a bivalent fragment comprising two Fab fragments linked by a disulfide bridge at the hinge region; (iii) a Fab' fragment, which is essentially a Fab with part of the hinge region (see, Fundamental Immunology (Paul ed., 3.sup.rd ed. 1993); (iv) a Fd fragment consisting of the $V_H$ and $C_H 1$ domains; (v) a Fv fragment consisting of the $V_L$ and $V_H$ domains of a single arm of an antibody; and (vii) a nanobody, a heavy chain variable region containing a single variable domain and two constant domains.

The term "antibody" as used herein is a synonym for "immunoglobulin." Antibodies according to the present invention may be whole immunoglobulins or fragments thereof, comprising at least one variable domain of an immunoglobulin, such as single variable domains, Fv (Skerra A. and Pluckthun, A. (1988) Science 240:1038-41), scFv (Bird, R. E. et al. (1988) Science 242:423-26; Huston, J. S. et al. (1988) Proc. Natl. Acad. Sci. USA 85:5879-83), Fab, (Fab')2 or other fragments well known to a person skilled in the art.

The term "single chain antibody" or "scFv" refers to a molecule comprising an antibody heavy chain variable region ($V_H$) and an antibody light chain variable region ($V_L$) connected by a linker. Such scFv molecules can have the general structures: $NH_2-V_L\text{-linker-}V_H-COOH$ or $NH_2-V_H\text{-linker-}V_L-COOH$.

As used herein, the term "functional property" is a property of a polypeptide (e.g., an immunobinder) includes, without limitation, the stability (e.g., thermal stability), solubility (e.g., in vivo and in cell culture), and antigen binding affinity.

The terms "specific binding," "selective binding," "selectively binds," and "specifically binds," refer to antibody binding to an epitope on a predetermined antigen. Typically, the antibody binds with an affinity ($K_D$) of approximately less than about $10^{-7}$ M, such as approximately less than about $10^{-8}$ M, $10^{-9}$ M or $10^{-10}$ M.

The term "nucleic acid molecule," refers to DNA molecules and RNA molecules. A nucleic acid molecule may be single-stranded or double-stranded, but preferably is double-stranded DNA. A nucleic acid is "operably linked" when it is placed into a functional relationship with another nucleic acid sequence. For instance, a promoter or enhancer is operably linked to a coding sequence if it affects the transcription of the sequence.

The term "vector," refers to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome.

The term "host cell" refers to a cell into which an expression vector has been introduced. Host cells can include bacterial, microbial, plant or animal cells. Bacteria, which are susceptible to transformation, include members of the enterobacteriaceae, such as strains of *Escherichia coli* or *Salmonella*; Bacillaceae, such as *Bacillus subtilis*; Pneumococcus; *Streptococcus*, and *Haemophilus influenzae*. Suitable microbes include *Saccharomyces cerevisiae* and *Pichia pastoris*. Suitable animal host cell lines include CHO (Chinese Hamster Ovary lines) and NS0 cells.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Various aspects of the invention are described in further detail in the following subsections. It is understood that the various embodiments may be combined at will.

Polypeptide Linkers

In one aspect, the invention provides polypeptides comprising two domains, wherein the domains are joined by an amino acid linker, and wherein the linker contains two cysteine residues that are capable of forming an intrachain disulphide bond. Such linkers are particularly advantageous in that they allow the site specific addition of a functional moiety (e.g., PEG), and/or the addition of one or more binding affinities to the polypeptide. The linkers of the invention are preferably genetically joined to a domain by genetic engineering, more preferably between two domains, thereby linking them to form a single polypeptide. Alternatively, the linkers of the invention can be chemically joined to a domain using any art recognized chemistry for effecting the joining of amino acids. Functional moieties can be connected to the linker by any art recognized chemistry. Preferably, they are connected to one or more cysteines being present in the linker.

In certain embodiments, the amino acid linker is of the general formula: $(X)_a$—C—$(X)_b$—C—$(X)_c$, where C is cysteine; X is any amino acid, including natural, non-natural amino acids, and chemical derivatives thereof; and, a, b, and c correspond the number of amino acids and can be any natural number. Preferably, a and c are numbers between 1-25, b is a number between 3-250. More preferably, a and c are numbers between 1-20, b is a number between 3-100.

In one embodiment, the linker comprises a peptide sequence in the loop forming region $X_b$. In said case, b is preferably any number of 3-30 amino acids, i.e. 3, 4, 5, 6, 7, 8, 9, 10, 11, 12, 13, 14, 15, 16, 17, 18, 19, 20, 21, 22, 23, 24, 25, 26, 27, 28, 29 or 30. Most preferably b is 7 or 12. Preferably, the loop forming region $X_b$ does not comprise a cysteine residue.

In certain embodiments, the linker comprises a polypeptide domain which is folded. In the general formula: $(X)_a$—C—$(X)_b$—C—$(X)_c$, b is preferably a number between 30 and 250, e.g. 50-200, 100-200, 125-225, 75-225, 125-225, such as 30, 40, 50, 60, 70, 80, 90, 100, 110, 120, 120, 130, 140, 150, 160, 170, 180, 190, 200, 210, 220, 230, 240 or 250. It is to be understood that any natural number in the indicated range is disclosed herewith. Accordingly, the amino acid linker is of the general formula $(X)_a$—C-domain-C—$(X)_b$, where C is cysteine; X is any amino acid, including natural, non-natural amino acids, and chemical derivatives thereof; domain is a domain as defined above; and, a, b correspond the number of amino acids and can be any natural number.

In certain embodiments, the amino acid linker is of the general formula: $(X)_{n=3-15}$—C—$(X)_{n=3-50}$—C—$(X)_{n=3-15}$ (SEQ ID No:1 in Table 1), where C is cysteine; X is any amino acid, including natural, non-natural amino acids, and chemical derivatives thereof; and, n is the number of amino acids. The number of amino acid residues in each region of the linker may be varied according to the structure of the polypeptide to which it is attached, provided that the cysteine residues in the linker are able to form an intrachain disulphide bond under non-reducing conditions. Moreover, the linker length and sequence must be such that the linker does not substantially impair one or more functional properties of the polypeptide to which it is a part. In a particular embodiment, the amino acid linker comprises the amino acid sequence set forth in any one of SEQ ID No:2, 3, and 4 (see Table 1).

The linkers of the invention are particularly well suited for joining VH and VL domains in scFv, especially those scFv that are highly stable and soluble, such as those described in WO09/000,098, the contents of which are incorporated herein by reference. The amino sequences of exemplary scFv polypeptides comprising the linkers of the invention are set forth in SEQ ID No:6 and 8 (see Table 1).

Polypeptides

The invention provides functionalized polypeptides, especially therapeutic polypeptides (e.g., scFv). The polypeptides of the invention comprise a linker sequence that can be rapidly and specifically functionalized by the addition of one or more functional moieties (e.g., PEG) and/or binding specificities (e.g., an amino acid sequence with a particular binding specificity).

Any polypeptide can be functionalized using the methods and compositions of the invention, including without limitation, polypeptides comprises an immunoglobulin domain (e.g., a VH or VL domain). In a particular embodiment, the polypeptide is an immunobinder, (e.g., an scFv).

In a preferred embodiment, polypeptides of the present invention are of the following general formula: domain 1-$(X)_a$—C—$(X)_b$—C—$(X)_c$-domain 2, where C is cysteine; domain 1 and 2 are domains as defined above; X is any amino acid, including natural, non-natural amino acids, and chemical derivatives thereof; and, a, b, and c are the number of amino acids. Preferably, domain 1 and 2 are $V_H$ and $V_L$ domains, or $V_L$ and $V_H$ domains, respectively.

Addition of Functional Moieties to Linkers

Figure 3:
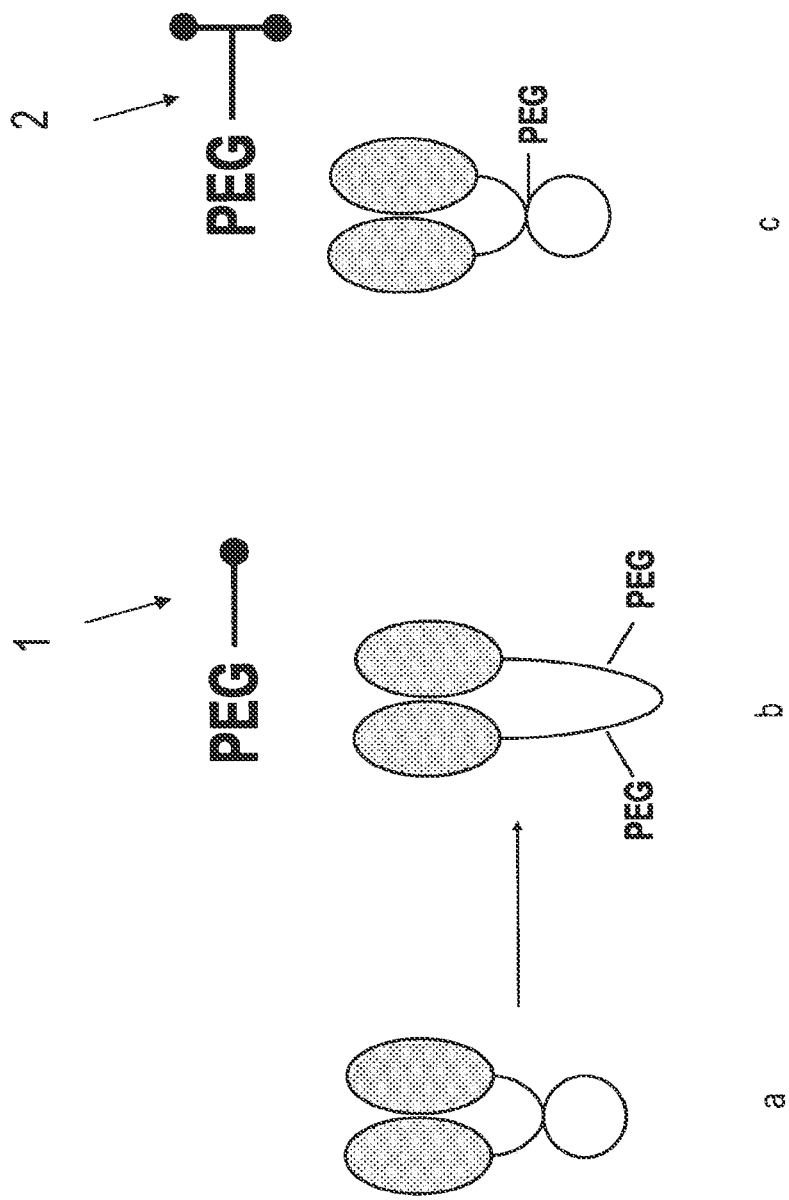

The linkers of the invention contain at least two cysteine residues that under non-reducing conditions form an intrachain disulphide bond (see FIG. 3). This disulphide bond allows the site specific addition of a functional moiety (e.g., PEG) to the linker using the methods described herein. Specifically, the cysteine residues in the disulphide bond can be covalently linked to a functional moiety (e.g., PEG). As the exposed cysteines allow for a much better directed pegylation, a manufacturing advantage over conventional PEG-attachment sites is achieved which often times yield a inhomogeneous population regarding the sites of PEG-attachment. If a functional moiety containing a monofunctional reactive group is employed, the functional moiety will become linked to a single cysteine residue. However, if a functional moiety containing a disulphide bond-specific bifunctional reactive group is employed, the functional moiety will become linked to both cysteine residues of an intrachain disulphide bond. Such bifunctional reagents are well known in the art and include, bis-sulfones (see e.g., Brocchini et al, Nature Protocols, 2006: 1(5), 241).

In certain embodiments, the invention provides a polypeptide comprising the amino acid sequence set forth in SEQ ID No:2, 3, 4, 6 and 8 (see Table 1), wherein at least one cysteine residue in the linker is covalently linked to a functional moiety (e.g., PEG). In other embodiments, the invention provides a polypeptide comprising the amino acid sequence set forth in SEQ ID No:2, 3, 4, 6 and 8 (see Table 1), wherein both cysteine residues in the linker are covalently linked to the same functional moiety (e.g., PEG) using a bifunctional reactive group, (e.g., a bis-sulfone).

Functionalization of Loops

Figure 5:
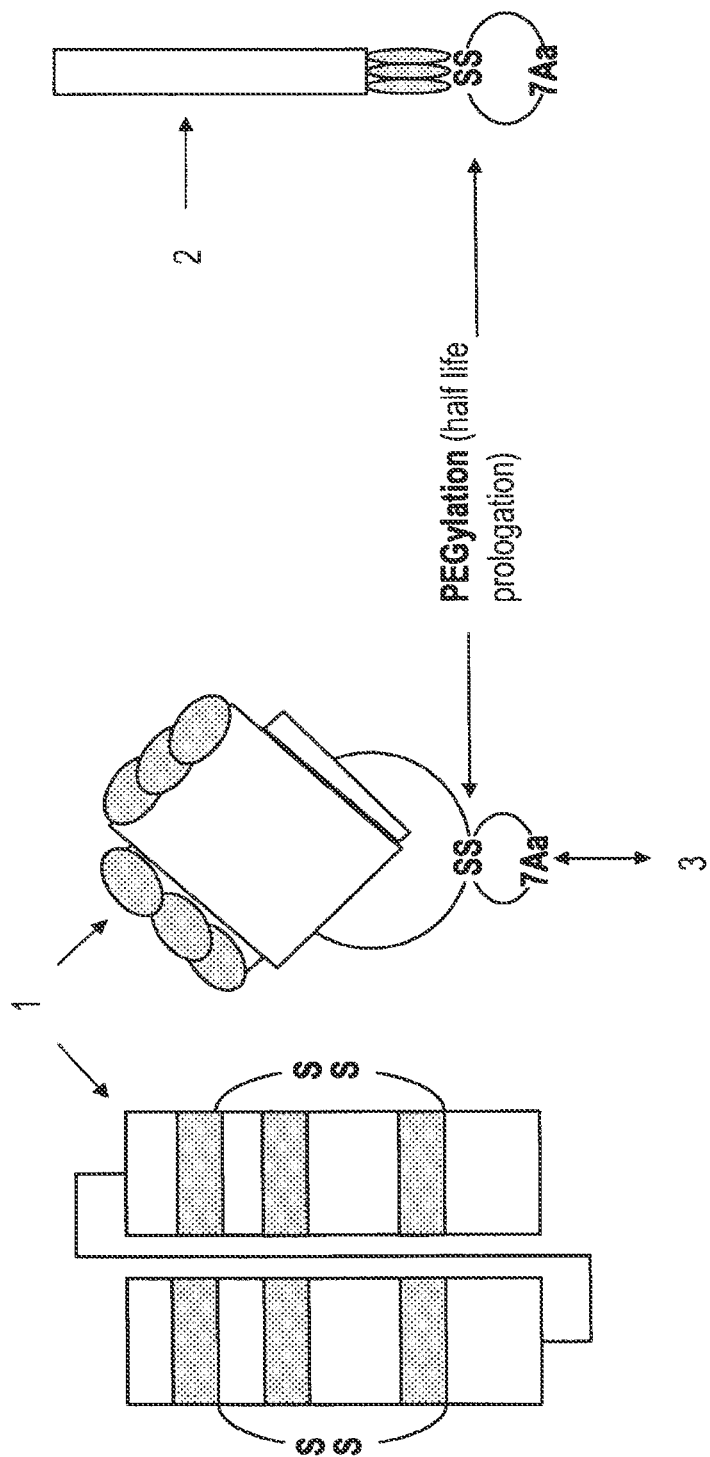

The formation of intrachain disulphide bonds by the cysteine residues in the linkers of the invention results in the cyclisation of the linker amino acid sequence between the cysteine residues to form a loop (see FIGS. 3 and 5). This loop structure is particularly advantageous in that it can be modified to comprise an amino acid sequence with one or more particular binding specificities, and hence add additional functionality to a polypeptide of which the loop is a part.

The loop sequence can e.g. have a binding specificity for any target molecule. Suitable target molecules include, without limitation, PK modifiers such, as hyaluronic acid, serum albumin, an integrin, an antibody Fc region, transferrin, and the like. For example, binding to serum albumin prolongs the half live of the polypeptide. Binding to FcRx improves the transport of the polypeptide into the placenta, whereas binding to mucin prolongs the residence time in the epithelium. In the case of an immunobinder with specificity for an antigen, in certain embodiments, the loop region between the VH and VL domains can be engineered to bind to the antigen and thus improve the affinity of the immunobinder. In another embodiment, the target molecule is the polypeptide itself. In other words, the loop can provide a multimerization function that causes the polypeptide to build dimers, trimers or higher order multimers. Multimers have a stronger avidity as compared to monomers. Furthermore, multimers allow for crosslinking and eventually followed by activation e.g. of receptors on the surface of a cell. In another embodiment, the target molecule is another immunobinder displaying a complementary loop in its linker i.e. the loops of the two molecules bind to each other, whereas the loops might be identical or different. This allows for the formation of bispecific or multispecific immunobinder complexes. Bispecific or multispecific complexes allow for recruiting molecules or cells to another cell or molecule, e.g. the recruitment of T cells to cancer cells results in the killing of the cancer cell (Cancer Res. volume 69 page 4941).

Any short amino acid sequence with a binding specificity for a desired target molecule can be introduced into the loops of the invention. In a preferred embodiment, the loop sequence consists of 5 to 15 amino acids (i.e. b is 5-15 in the general formula $(X)_a$—C—$(X)_b$—C—$(X)_c$) and contains no cysteines. Suitable amino acid sequences that can be incorporated into a loop include, without limitation, a hyaluronic acid binding peptide (e.g., a peptide comprising residues 12 to 23 of SEQ ID No:4 in Table 1), and an integrin binding peptide (e.g., an RGD peptide).

New peptides with binding specificities to desired target molecules, suitable for incorporation into a loop, can be identified by art recognized means such as, for example, phage display, yeast display and mRNA display. Such display systems are well known in the art (see, for example, U.S. Pat. Nos. 66,258,558, 6,699,658; and 7,118,879, which are hereby incorporated by reference). By way of example, to perform a phage display screen, the loop formed by the two cysteines of the linker can be fused to a phage capsid protein for display on a phage surface (see FIG. 5 for a schematic drawing). The loop sequence, which ideally comprises between 5-15 amino acids and contains no cysteines other than those required to form the loop, is randomized to provide a library of loop sequences to screen. Suitable phage libraries are commercially available, e.g. the disulfide-constrained heptapeptide (Ph.D.-C7C) library from New England Biolab. Target molecules for such phage screens include, for example, PK modifiers, such as, collagen type II, albumin, antibody Fc regions, antibody Fc receptors (e.g., FcRx), mucins, integrins, tight junction proteins and complement factors.

Modified Polypeptides

Additionally or alternatively, the polypeptides of the invention can be covalently linked to a functional moiety (e.g., PEG) at one or more amino acid residues outside of the linker region. Any amino acid residue that does not substantially impair one or more functional properties of the polypeptide can be employed, for example, surfaced exposed lysine and cysteine residues. If desired, a polypeptide can be modified (by addition or substitution) to introduce additional reactive amino acids, suitable for linkage to a functional moiety. In a particular embodiment, a polypeptide is modified to contain at least one pair of cysteine residues, and wherein at least one pair of the cysteine residues form an intrachain disulfide bond in the mature polypeptide. A functional moiety can be linked to a single reactive residue (e.g., a cysteine) using a monofunctional reactive group, or linked to two disulphide bonded cysteines using a bifunctional disulphide bond-specific reactive group (e.g., a bis-sulfone).

Accordingly, in one embodiment, the invention provides a polypeptide comprising the amino acid sequence set forth in SEQ ID No. 5, wherein at least one amino acid residue selected from the group consisting of Lys40, Lys43, Lys46, Lys107, Lys176, Lys197 and Lys208 is covalently linked to a functional moiety (e.g., PEG).

In another embodiment, the invention provides a polypeptide comprising the amino acid sequence set forth in SEQ ID No. 5, wherein at least one pair of cysteine residues selected from the group consisting of C24-C89 and C154-C228 is covalently linked to the same functional moiety (e.g., PEG).

In another embodiment, the invention provides a polypeptide comprising the amino acid sequence set forth in SEQ ID No. 6, wherein at least one amino acid residue selected from the group consisting of Cys123 and Cys136 is covalently linked to a functional moiety (e.g., PEG).

In another embodiment, the invention provides a polypeptide comprising the amino acid sequence set forth in SEQ ID No. 6, wherein the pair of cysteine residues Cys123-Cys136 is covalently linked to the same functional moiety (e.g., PEG).

In another embodiment, the invention provides a polypeptide comprising the amino acid sequence set forth in SEQ ID No. 7, wherein at least one amino acid residue selected from the group consisting of Lys44, Lys47, Lys105, Lys109, Lys142, Lys143, Lys149, Lys173, Lys193 and Lys195 is covalently linked to a functional moiety (e.g., PEG).

In another embodiment, the invention provides a polypeptide comprising the amino acid sequence set forth in SEQ ID No. 7, wherein at least one pair of cysteine residues selected from the group consisting of Cys25-Cys90 and Cys152-Cys226 is covalently linked to the same functional moiety (e.g., PEG).

In another embodiment, the invention provides a polypeptide comprising the amino acid sequence set forth in SEQ ID No. 8, wherein at least one amino acid residue selected from the group consisting of Cys121 and Cys129 is covalently linked to a functional moiety (e.g., PEG).

In another embodiment, the invention provides a polypeptide comprising the amino acid sequence set forth in SEQ ID No. 8, wherein the pair of cysteine residues Cys121-Cys129 is covalently linked to the same functional moiety (e.g., PEG).

In another embodiment, the invention provides a polypeptide, comprising the amino acid sequence set forth in SEQ ID No. 5, 6, 7, or 8, wherein the polypeptide is modified to contain at least one reactive amino acid (e.g., cysteine or lysine). Such reactive amino acids can be covalently linked to a functional moiety (e.g., PEG).

In another embodiment, the invention provides a polypeptide comprising the amino acid sequence set forth in SEQ ID No. 5, 6, 7, or 8, wherein the polypeptide is modified to contain at least one pair of cysteine residues, and wherein at least one pair of cysteine residues are capable of forming an intrachain disulphide bond in the mature polypeptide. In a particular embodiment, at least one pair of cysteine residues are covalently linked to the same functional moiety (e.g., PEG) bifunctional reactive group (e.g., a bis-sulphone).

As known in the art, the attachment of PEG improves certain characteristics of biopharmaceuticals without altering their function, thereby enhancing their therapeutic effect. Exemplary effects are (i) improved pharmacokinetics through enhanced solubility, improved stability, sustained absorption and/or continuous biopharmaceutical action; (ii) increased circulation time which decreases the therapeutically effective amount and/or the dosing frequency; and/or (iii) decreased toxicity, e.g. due to an improved safety profile, a reduced immunogenicity, a reduced antigenicity and/or reduced proteolysis.

Polypeptide Compositions and Formulations

Another aspect of the invention pertains to pharmaceutical formulations of the polypeptide (e.g. ScFv) compositions of the invention. Such formulations typically comprise the polypeptide (e.g. ScFv) composition and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for, for example, intravenous, intramuscular, subcutaneous, topical (e.g., to eye, skin, or epidermal layer), inhalation, parenteral, spinal or epidermal administration (e.g., by injection or infusion). Depending on the route of administration, the polypeptides (e.g. ScFv) may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

TABLE 1

Linker and scFv sequences

| SEQ ID NO: | Linker | Sequence |
|---|---|---|
| 1 | SS linker | $(X)_{3-15}C(X)_{3-50}C(X)_{3-15}$ |
| 2 | SS linker | GGGGSGGGGSC$(X)_{3-50}$CGGGGSGGGGS |
| 3 | SS linker | GGGGSGGGGSCGGGSGGGCGGGGSGGGGS |
| 4 | SS Pep-1 linker | GGGGSGGGGSCGAHWQFNALTVRCGGGGSGGGGS |
| 5 | ESBA903 Normal linker | MEIVMTQSPSTLSASVGDRVIITCQASEIIHSWLAWYQQKPGKA PKLLIYLASTLASGVPSRFSGSGSGAEFTLTISSLQPDDFATYY CQNVYLASTNGANFGQGTKLTVLGGGGSGGGGSGGGGSGGGGS EVQLVESGGGLVQPGGSLRLSCTASGFSLTDYYYMTWVRQAPGK GLEWVGFIDPDDDPYYATWAKGRFTISRDTSKNTVYLQMNSLRA EDTAVYYCAGGDHNSGWGLDIWGQGTLVTVSS |
| 6 | ESBA903 SS Pep-1 linker | MEIVMTQSPSTLSASVGDRVIITCQASEIIHSWLAWYQQKPGKA PKLLIYLASTLASGVPSRFSGSGSGAEFTLTISSLQPDDFATYY CQNVYLASTNGANFGQGTKLTVLGGGGSGGGGSCGAHWQFNAL TVRCGGGGSGGGGSEVQLVESGGGLVQPGGSLRLSCTASGFSLT DYYYMTWVRQAPGKGLEWVGFIDPDDDPYYATWAKGRFTISRDT SKNTVYLQMNSLRAEDTAVYYCAGGDHNSGWGLDIWGQGTLVTV SS |
| 7 | ESBA105 Normal linker | MADIVMTQSPSSLSASVGDRVTLTCTASQSVSNDVVWYQQRPGK APKLLIYSAFNRYTGVPSRFSGRGYGTDFTLTISSLQPEDVAVY YCQQDYNSPRTFGQGTKLEVKRGGGGSGGGGSGGGGSSGGGSQV QLVQSCAEVKKPCASVKVSCTASCYTFTHYCMNWVRQAPCKCLE WMGWINTYTGEPTYADKFKDRFTFSLETSASTVYMELTSLTSDD TAVYYCARERGDAMDYWGQGTLVTVSS |
| 8 | ESBA105 SS linker | MADIVMTQSPSSLSASVGDRVTLTCTASQSVSNDVVWYQQRPGK APKLLIYSAFNRYTGVPSRFSGRGYGTDFTLTISSLQPEDVAVY YCQQDYNSPRTFGQGTKLEVKRGGGGSGGGGSCGGGSGGGCGGG GSGGGGSQVQLVQSGAEVKKPGASVKVSCTASGYTFTHYGMNWV RQAPGKGLEWMGWINTYTGEPTYADKEKDRFTESLETSASTVYM ELTSLTSDDTAVYYCARERGDAMDYWGQGTLVTVSS |

EXEMPLIFICATION

The present disclosure is further illustrated by the following examples, which should not be construed as further limiting. The contents of all figures, references, patents and published patent applications cited throughout this application are expressly incorporated herein by reference in their entireties.

In general, the practice of the present invention employs, unless otherwise indicated, conventional techniques of chemistry, molecular biology, recombinant DNA technology, and immunology (especially, e.g., immunoglobulin technology). See, e.g., Sambrook, Fritsch and Maniatis, Molecular Cloning: Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., C. S. H. L. Press, Pub. (1999); Current Protocols in Molecular Biology, eds. Ausubel et al., John Wiley & Sons (1992). See also, e.g., Polytherics US6803438; EP1701741A2; EP1648518A2; WO05065712A2; WO05007197A2; EP1496941A1; EP1222217B1; EP1210093A4; EP1461369A2; WO03089010A1; WO03059973A2; and EP1210093A1); Genentech US20070092940A1 and EP1240337B1; and ESBATech U.S. Ser. No. 60/899,907 and WO03097697A2.

PEGylation of ESBA105

Methyl-PEO$_{12}$-Malemide (Pierce), a sulfhydryl-reactive PEGylation reagent was used for modification of sulfhydryl groups in ESBA105 (SEQ ID No:7) and ESBA105-SS-LINKER (SEQ ID No:8). Since ESBA105 contains cysteine residues whose side-chain sulfur atoms occur in pairs as disulfide bonds, reduction of these disulfide bonds is required to expose the sulfhydryl groups that serve as a target for PEGylation with Methyl-PEO$_{12}$-Malemide. Pegylation of ESBA105 and ESBA105-SS-LINKER was performed as recommended by the supplier of PEG (Thermo Scientific: Pierce Protein Research Products). Shortly, disulfide bonds were reduced by incubation of approximately 2 mg of ESBA105 in the presence of 20 mM DTT for 30 minutes at 4° C. For removal of DTT the reduced ESBA105 was dialysed against PBS (pH 6.5) using Slide-A-Lyzer Dialysis cassettes (Pierce; cut-off: 7000 Da). After dialysis and up-concentration, 2 mg/ml of protein was pegylated by incubation of a 20-fold molar excess of Methyl-PEO$_{12}$-Malemide at 4° C. overnight. The labeled proteins were purified from nonreacted Methyl-PEO$_{12}$-Malemide by dialysis using Slide-A-Lyzer Dialysis cassettes (Pierce; cut-off: 7000 Da).

SDS-PAGE

SDS-PAGE was performed under non-reducing conditions using the commercially available Bis-Tris electrophoresis system from Invitrogen according to the recommendations of the provider. 5 μg of protein samples were loaded on precast 12% Bis-Tris gels. The gels were stained using Coomassie reagent (0.1% (w/v) Coomassie G250, 10% glacial acetic acid, 50% ethanol) for 15 minutes. Destaining was done using 10% (v/v) acetic acid.

Western Blot Analysis to Confirm Pegylation 1, 10 and 100 ng of PEGylated ESBA105-SS-LINKER was loaded on a precast 12% Bis-Tris gel. Samples were blotted on nitrocellulose membranes and the PEG moiety was detected with a rabbit monoclonal anti-PEG antibody (Epitomics). After incubation with the primary antibody, membranes were incubated with horseradish peroxidase (HRP)-conjugated goat anti-rabbit polyclonal antibody (Santa Cruz). Specific binding of antibodies to the membranes was detected by a chemiluminescence detection system (Pierce).

Direct ELISA to Confirm Binding of Pegylated ESBA105 to Human TNF Alpha

Binding of ESBA105 and its derivatives was assessed by a direct ELISA. Human TNF alpha (PeproTech EC Ltd) was coated on a 96-well microtitre plate and then blocked using BSA (bovine serum albumin). ESBA105 and ESBA105 derivates were tested at concentrations of 50 nM, 12.5 nM, 3.13 nM, 1.56 nM, 0.78 nM, 0.39 nM, 0.20 nM, 0.10 nM and 0.05 nM. Binding of ESBA105 and its derivatives to human TNF alpha was visualized by the subsequent addition of a biotinylated rabbit polyclonal anti-ESBA105 antibody (AK3A, generated at ESBATech), streptavidin Poly HRP and a chromogenic substrate (POD). The product of this reaction was detected by measurement of the optical density (OD) at 450 nM using a spectrophotometer. Data were analyzed using a 4-parameter logistic curve fit, and $EC_{50}$ values were calculated from the dose-response curves of the scFvs.

Surface Plasmon Resonance Analysis of ESBA903 and ESBA903 with Pep1 in the Linker For binding affinity measurements, surface Plasmon resonance measurements with BIAcore™-T100 were employed. In these experiments, purified *Escherichia coli*-expressed recombinant human $VEGF_{165}$ (PeproTech EC Ltd) was used. Carboxymethylated dextran biosensor chips (CM4, GE Healthcare) were activated with N-ethyl-N'-(3-dimethylaminopropyl)carbodiimide hydrochloride and N-hydroxysuccinimide according to the supplier's instructions. Human $VEGF_{165}$ was coupled to 1 of the 4 different flow cells on a CM4 sensor chip using a standard amine-coupling procedure. The range of responses obtained with the immobilized $hVEGF_{165}$ molecule after coupling and blocking was approximately 120-140 response units (RU). The 4th flow cell of each chip was treated similarly except no proteins were immobilized prior to blocking, and the flow cell was used as in-line reference. Various concentrations of anti-VEGF scFvs (20 nM, 10 nM, 5 nM, 2.5 nM, 1.25 nM, 0.63 nM, 0.31 nM and 0.16 nM) in HBS-EP buffer (0.01 M HEPES, pH 7.4, 0.15 M NaCl, 3 mM EDTA, 0.005% surfactant P20) were injected into the flow cells at a flow rate of 30 μl/min for 5 min. Dissociation of the anti-VEGF scFv from the VEGF on the CM4 chip was allowed to proceed for 10 min at 25° C. Sensorgrams were generated for each anti-VEGF scFv sample after in-line reference cell correction followed by buffer sample subtraction. The apparent dissociation rate constant ($k_d$), the apparent association rate constant ($k_a$) and the apparent dissociation equilibrium constant ($K_D$) were calculated using one-to-one Langmuir binding model with BIAcore T100 evaluation Software version 1.1.

Cloning and Expression of scFvs

The scFvs described and characterized herein were produced as follows. In some cases DNA sequences encoding for the various scFvs were de novo synthesized at the service provider Entelechon GmbH (www.entelechon.com). The resulting DNA inserts were cloned into the bacterial expression vector pGMP002 via NcoI and HindIII restriction sites introduced at the 5' and 3' end of the scFv DNA sequence, respectively. In some cases the modified linkers were introduced by state-of-the-art methods as annealed, complementary oligos that encode the respective amino acid molecules, by cloning them into suitable restriction sites between the VH and VL domains. In other cases, point mutations were introduced into the VH and/or VL domain using state of the art assembling PCR methods. The cloning of GMP002 is described in Example 1 of WO2008006235. The production of the scFvs was performed as described for ESBA105 in Example 1 of WO08/006,235, which is hereby incorporated by reference.

EXAMPLE 1

Pegylation of ESBA105 and ESBA105-Ss-Linker

ESBA105 (SEQ ID No: 7) is a single chain antibody that specifically binds and inhibits human TNFalpha (see e.g. WO 06/131013, which is hereby incorporated by reference).

ESBA105-SS-linker (SEQ ID No: 8) is an ESBA105 variant, in which the linker was replaced by the SS-linker (SEQ ID No:3).

ESBA105, ESBA105 reduced with DTT, ESBA105 reduced and subjected to cysteine pegylation and ESBA105 reduced and subjected to cysteine pegylation followed by dialysis were analyzed by SDS-PAGE. Upon pegylation of the protein an increase of molecular weight of approximately 4 kDa is expected. "ESBA105 reduced" and "ESBA105 reduced cysteine-pegylated" migrate at a slightly higher position compared to ESBA105. Upon dialysis of cys pegylated ESBA105, the protein migrates at the same position as ESBA105 suggesting that the protein shift was not due to pegylation but rather due to reduction of the disulfide bonds that were formed again upon oxidation of the sulfhydryl groups during dialysis. These data indicate that the reduced intramolecular cysteines (SH) of ESBA105 have low accessibility for PEG-NHS. In contrast to the sulfhydryl grougs of the intramolecular cysteines in ESBA105, primary amines (Lysine residues at the N-terminus) are accessible for PEG-NHS, as shown in lane 6 and 7 of FIG. 1.

Figure 1:
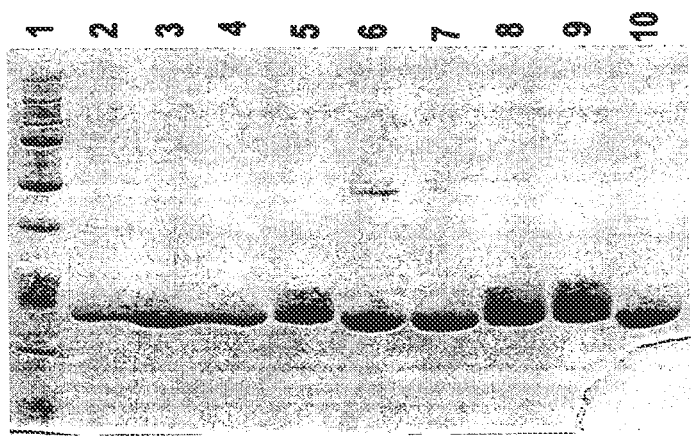
Figure 2:
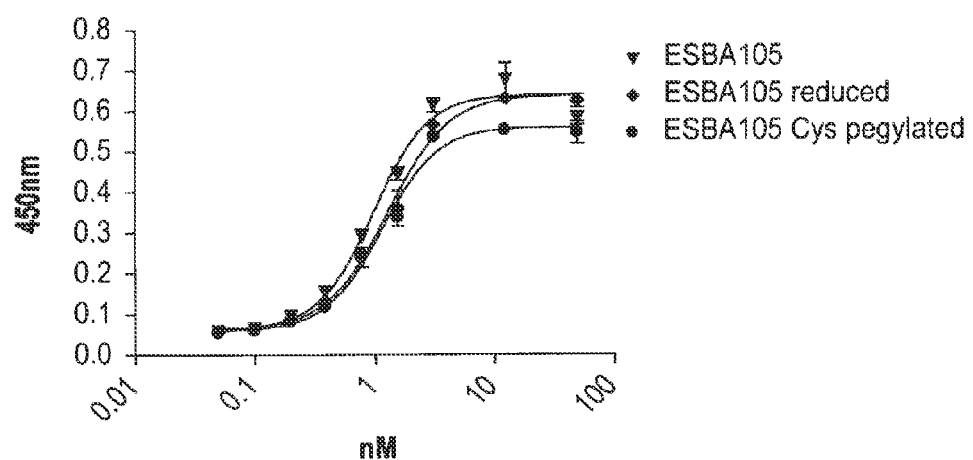
Figure 2:
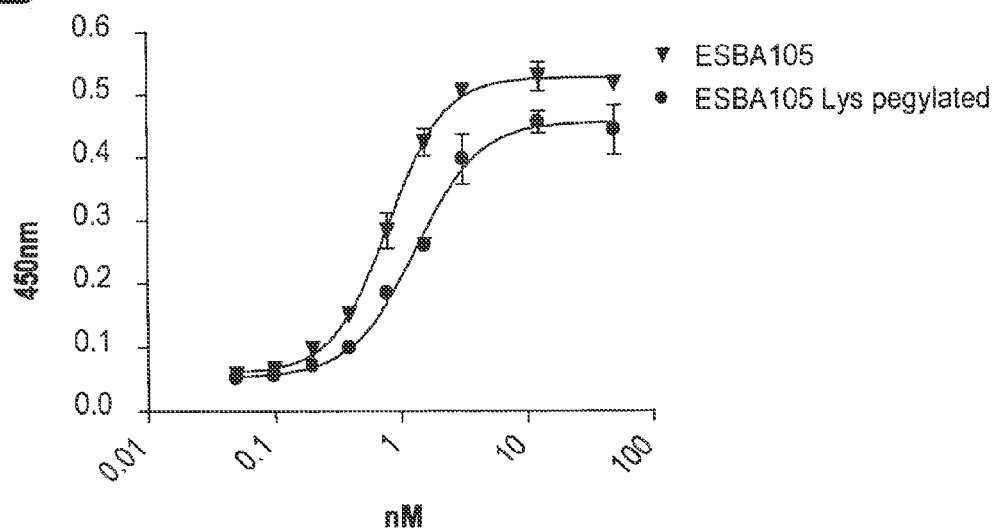

The activities of differently treated ESBA105 preparations as described above were assessed in ELISA experiments. The ELISA analysis depicted in FIG. 2 show that reduced ESBA105 is as active as oxidized ESBA105. Cys pegylated ESBA105 shows only a slight loss of binding activity compared to ESBA105. However, as shown in FIG. 1 the extent of PEGylation of intrachain disulfides in ESBA105 is low. Lys-pegylation was successful with only minor loss of binding activity towards human TNF alpha.

Figure 4:
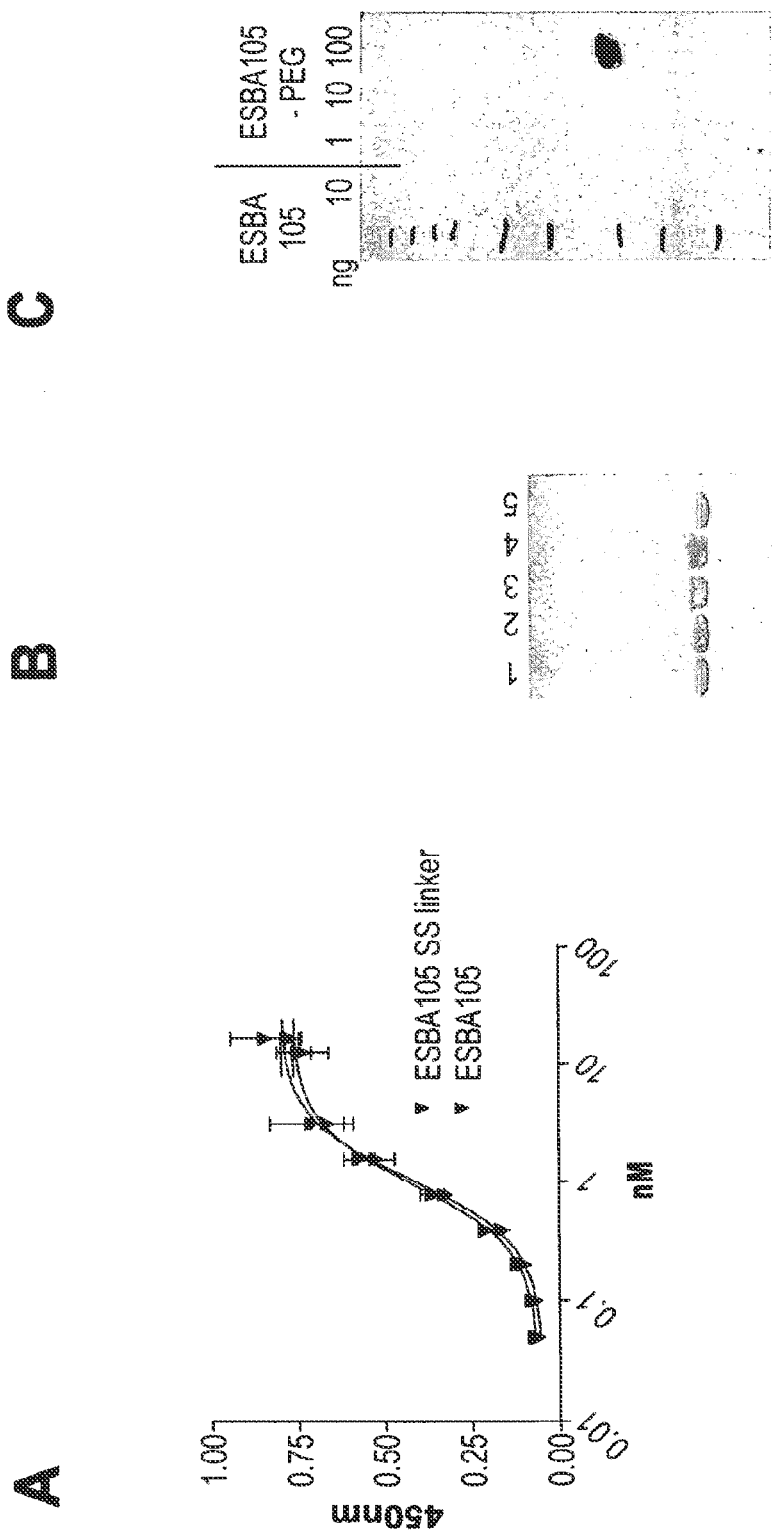
Figure 6:
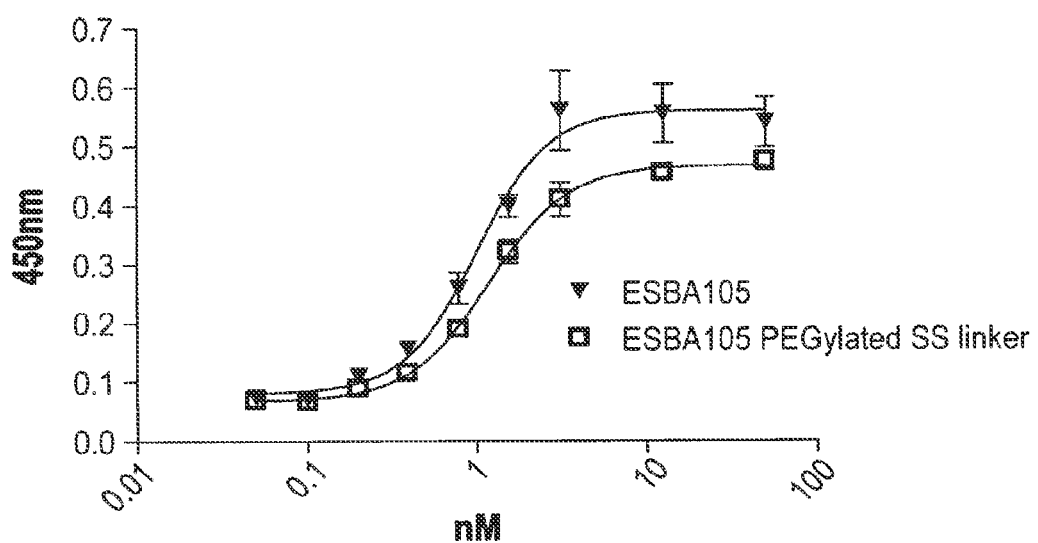

One purpose of the present invention was to provide scFv antibodies that are susceptible to cys-pegylation. In a first step, it was examined, whether the un-pegylated ESBA105-SS-linker molecule is still active as compared to ESBA105. Once this was confirmed by means of an ELISA assay as depicted in FIG. 4A, ESBA105-SS-linker was subjected to cys-pegylation. To test for successful cys-pegylation, ESBA105-SS-linker, reduced ESBA105-SS-linker, reduced cys pegylated ESBA105-SS-linker and cys pegylated ESBA105-SS-linker subjected to dialysis were analyzed by SDS-PAGE (see FIG. 4B). PEGylated ESBA105-SS-linker migrates at a higher position compared to ESBA105-SS-linker indicating successful PEGylation of ESBA105-SS-linker. PEGylation of ESBA105-SS-linker was confirmed by Western blot analysis using a rabbit anti-PEG monoclonal antibody (see FIG. 4C). A signal at the expected size was detected with 100 ng/ml pegylated ESBA105-SS-linker. Furthermore, the ELISA assay as depicted in FIG. 6 confirms that cys-pegylated ESBA105-SS-linker almost fully active as compared to naked ESBA105.

Conventional cys-pegylation of the ESBA105 SS-linker using a PEG with a monospecific reactive group is depicted schematically on FIG. 3 (middle). An alternative method of cys-pegylation is also depicted in FIG. 3 (right). This, latter, method employs a PEG attached to a bifunctional reactive group (schematically represented as a horizontal "T" having a PEG molecule on its left end), which allows connection of a PEG molecule to both cysteine residues of a disulphide bond in a protein. Such linker technology is described by Shaunak et al. Nature Chemical Biology 2006, volume 2 page 312; Brocchini et al, Nature Protocols, 2006: 1(5), 241, and WO05/007197.

EXAMPLE 2

Introduction of a Binding Activity into the Ss-Linker

A second application of the present invention is to introduce an additional binding specificity into polypeptides (e.g., scFv). In this example, the Pep-1 peptide, which was identified to bind to hyaluronic acid during a phage display selection (Mummert et al. J. Exp. Med. 2000, volume 192, page 769), was introduced into the loop region of the SS linker to give rise to the SS Pep1 linker (SEQ ID NO:4). The SS Pep1 linker was introduced into the scFv ESBA903 to produce ESBA903 SS Pep1 linker (sometimes also referred to as ESBA903-Pep1; SEQ ID NO:6). As demonstrated by the surface plasmon resonance results shown in FIG. 7, ESBA903-Pep1 displaying the Pep1 12mer peptide in its loop, binds equally well to its target (VEGF) as unmodified ESBA903 (SEQ ID No: 5), and therefore is still fully functional (Kd values measured were 4.436E-11 M and 5.608E-11 M, respectively). ESBA903-Pep1 was designed to prolong the local half-life as compared to naked ESBA903 when applied to a site where hyaluronic acid is present, for example such as the vitreous body or a joint.

Equivalents

Those skilled in the art will recognize, or be able to ascertain using no more than routine experimentation, many equivalents to the specific embodiments of the invention described herein. Such equivalents are intended to be encompassed by the following claims.

I claim:

1. An isolated nucleic acid molecule encoding a polypeptide comprising a single chain antibody (scFv) comprising an antibody VH and an antibody VL domain that are connected by an amino acid linker; wherein the linker comprises two cysteines capable of forming an intrachain disulphide bond, and wherein the amino acids between the cysteines in the linker sequence form a loop when the two cysteines are disulphide bonded to one another.

2. The isolated nucleic acid molecule of claim 1, wherein the linker comprises the amino acid sequence set forth in SEQ ID No. 1.

3. The isolated nucleic acid molecule of claim 1, wherein the linker comprises the amino acid sequence set forth in SEQ ID No. 2.

4. The isolated nucleic acid molecule of claim 1, wherein the loop binds to a target molecule.

5. The isolated nucleic acid molecule of claim 4, wherein the target molecule is a PK modifier.

6. The isolated nucleic acid molecule of claim 4, wherein the PK modifier is serum albumin.

7. The isolated nucleic acid molecule of claim 4, wherein the PK modifier is a hyaluronic acid.

8. The isolated nucleic acid molecule of claim 1, wherein the linker comprises the amino acid sequence set forth in SEQ ID No. 3.

9. The isolated nucleic acid molecule of claim 1, wherein the linker comprises the amino acid sequence set forth in SEQ ID No. 4.

10. The isolated nucleic acid molecule of claim 1, wherein the polypeptide is an immunobinder.

11. The isolated nucleic acid molecule of claim 10, wherein the polypeptide is a scFv.

12. The isolated nucleic acid molecule of claim 1, wherein the polypeptide has the amino acid sequence set forth in SEQ ID No. 6 or 8.

13. The isolated nucleic acid molecule of claim 1, wherein at least one cysteine residue in the linker is covalently linked to a functional moiety.

14. The isolated nucleic acid molecule of claim 1, wherein the two cysteine residues in the linker are covalently linked to the same functional moiety.

15. The isolated nucleic acid molecule of claim 13 or 14, wherein the functional moiety is PEG.

16. An expression vector comprising the nucleic acid molecule of claim 1.

17. A host cell comprising the expression vector of claim 16.

* * * * *